(12) United States Patent
Orten

(10) Patent No.: US 7,368,855 B2
(45) Date of Patent: May 6, 2008

(54) PIEZOELECTRIC VIBRATION SENSOR

(75) Inventor: Birger Orten, Ålesund (NO)

(73) Assignee: Vibrotron AS, Vettre (NO)

( * ) Notice: Subject to any disclaimer, the term of this patent is extended or adjusted under 35 U.S.C. 154(b) by 375 days.

(21) Appl. No.: 10/510,623

(22) PCT Filed: Apr. 7, 2003

(86) PCT No.: PCT/NO03/00111

§ 371 (c)(1),
(2), (4) Date: Mar. 11, 2005

(87) PCT Pub. No.: WO03/087737

PCT Pub. Date: Oct. 23, 2003

(65) Prior Publication Data

US 2005/0156486 A1 Jul. 21, 2005

(30) Foreign Application Priority Data

Apr. 8, 2002 (NO) .................................. 20021666

(51) Int. Cl.
*H04R 17/00* (2006.01)
*H01L 41/04* (2006.01)
(52) U.S. Cl. .................................. 310/328; 310/323.21
(58) Field of Classification Search ................. 310/324, 310/330–332, 334, 323.21
See application file for complete search history.

(56) References Cited

U.S. PATENT DOCUMENTS

| 3,792,204 A | 2/1974 | Murayama et al. |
| 3,947,644 A | 3/1976 | Uchikawa |
| 4,186,323 A * | 1/1980 | Cragg et al. ................ 310/324 |
| 6,438,242 B1 | 8/2002 | Howarth |

FOREIGN PATENT DOCUMENTS

| DE | 29 14 608 | 10/1980 |
| DE | 32 47 574 | 6/1984 |
| DE | 32 48 222 | 6/1984 |
| EP | 0 557 780 | 9/1993 |

* cited by examiner

*Primary Examiner*—J. San Martin
(74) *Attorney, Agent, or Firm*—Wenderoth, Lind & Ponack, L.L.P.

(57) ABSTRACT

A sensor unit for picking up mechanical vibrations, sound and ultrasound has at least one piezoelectric foil strip (piezo strip) as a sensor element. The piezo strip has signal wires attached thereto for transporting out electrical signals representing vibration, sound or ultrasound that have been picked up. The piezo strip is, at two opposite ends, attached to flat support parts, and at least one engagement strip of for instance plastic material is attached in the same support parts to extend in curved-out fashion along the piezo strip, thereby to provide at least one space between the strips. Several sensor units can be mounted together in a frame to constitute a sheet with a sensor matrix.

20 Claims, 7 Drawing Sheets

Figure 1:
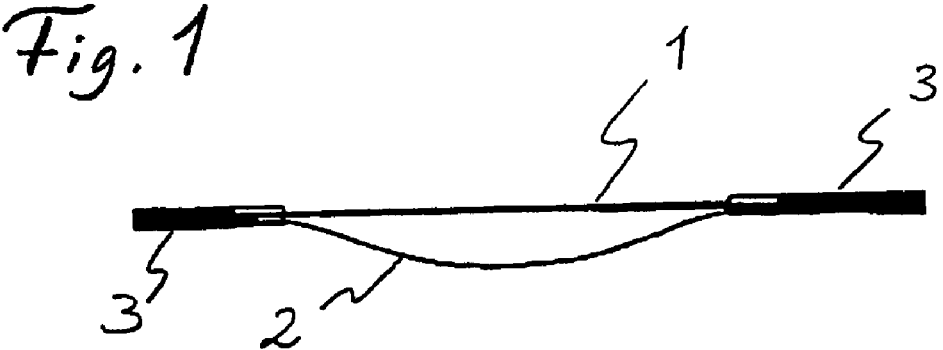

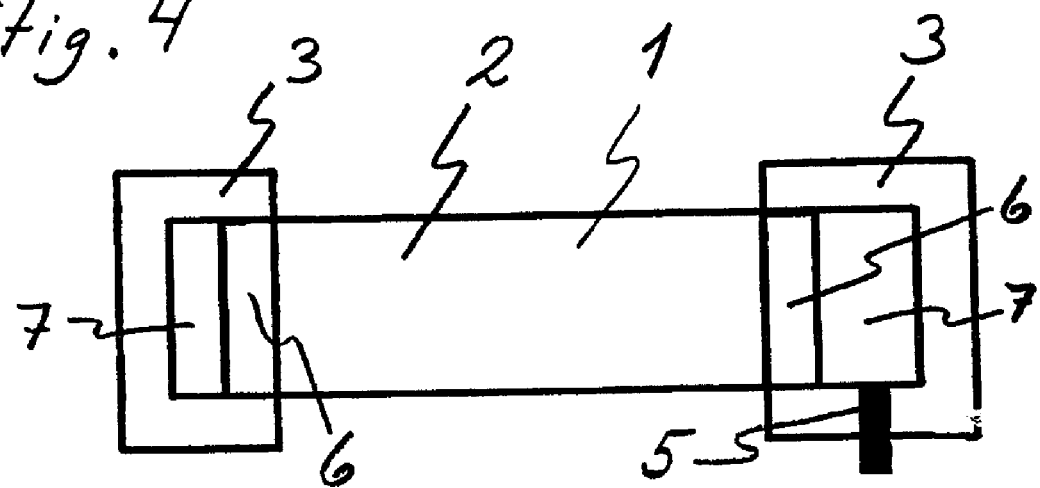
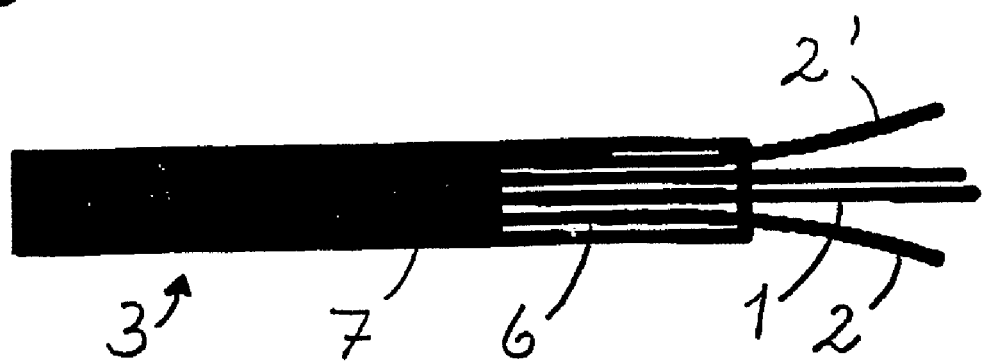

PIEZOELECTRIC VIBRATION SENSOR

BACKGROUND OF THE INVENTION

The present invention relates in general to sensing of mechanical vibrations, possibly in the form of sound or ultrasound, by means of one or several sensor units having a piezoelectric foil as a signal-delivering element. More particularly, the invention relates to a sensor unit for picking up mechanical vibrations, sound, and ultrasound. In further aspects, the invention relates to a vibration detector array with a plurality of sensor units. Finally, the invention relates to uses of such vibration detector arrays.

Particularly within the art of auscultation, i.e. the art concerning listening for sounds generated in living bodies, for instance heart sounds, many different sensor types have been developed for use by e.g. a doctor, for examination purposes. In this connection, reference is made to previous patent publications regarding auscultation and sensor technology belonging to the owner of rights to the present invention, see for instance Norwegian patents 300250, 304870 and 306926. The present invention is primarily directed to this type of examination, and aims particularly at being able to prepare a mapping of an area in a living body on the basis of a matrix investigation. In other words, sound/vibration picked up by plural sensors, is converted to separate signals to be led into a computer that provides systematizing of the sound/ultrasound image in order to prepare a composite mapping of the sound that is received from a large area, for instance an area of the back of a person, or a chest area.

But, in addition to the above, there are also industrial areas of use. For instance, it is possible to undertake a vibration analysis of underlying structures by means of a sensor matrix laid down on a metal surface of a machine construction or similar device.

However, the invention does not concern signal processing or algorithms in connection therewith, but deals with special sensor elements intended to be included in larger sensor groups or arrays, possibly sensor matrices, and the composition of such sensor groups.

SUMMARY OF THE INVENTION

Hence, in a first aspect of the present invention, there is provided a sensor unit for picking up mechanical vibrations, sound and ultrasound, having at least one piezoelectric foil strip (piezo strip) as a sensor element. The piezo strip has signal wires attached for exporting electric signals representing vibration, sound or ultrasound being picked up. The sensor unit in accordance with the invention is characterized in that the piezo strip is, at two opposite ends, held in flat support parts, and in that at least one engagement strip for receiving vibrations and propagating them to said piezo strip is held in the same support parts so as to extend in a curved manner along the piezo strip, thereby to provide at least one space between the strips.

In a preferred embodiment of the invention, the support parts are separate support pieces having holding details for the strips, for instance pockets.

In another preferred embodiment, the sensor unit comprises two such engagement strips, one outside each flat side of the piezo strip.

The further (engagement) strip/strips may be a little stiff, and will then automatically tend to stretch the piezo strip.

Also, the engagement strip/strips may be held loosely in at least one of the support parts, by being inserted into a pocket.

In an important embodiment of the invention, the space between the piezo strip and the engagement strip is occupied by a substance with the ability to transfer pressure, for instance a silicon substance. The piezo strip and the engagement strip are substantially symmetrically curved outwards centrally to bound the substance.

In another embodiment of the invention, the support parts are constituted by welding rims for a bubble consisting of two semi-ovoid foil pieces, and the at least one engagement strip constitutes at least one of the two foil pieces. The piezo strip may then be arranged outstretched in the space right in between the two foil pieces. In addition, the piezo strip may be attached along the whole welding rim, thereby to constitute a boundary between two closed spaces. At least one of the two closed spaces may be filled by a substance having the ability to transfer a pressure. One of the substances may have a hardness value of the same magnitude as body tissue in an area in and under the skin in a topical listening area on a human body or animal body.

In another aspect of the invention there is, as mentioned in the introduction, a vibration detector array comprising a number of sensor units arranged in a substantially planar a×b-matrix with a units along one direction and b units along a perpendicular direction in the plane, and with separate signal wires going out from each separate sensor unit. The vibration detector array according to this aspect of the invention is characterized in that each sensor unit is constructed such as stated in any one of the above embodiments that do not relate to a bubble shape, and that each sensor unit is attached in a common surrounding frame.

The frame may then be designed with b parallel openings, in which openings of the sensor units are mounted by means of a common support piece constituting a boundary edge for each opening, for one end of the a sensor units, while the other end of each one of the a sensor units hangs freely in the opening.

In accordance with a further aspect of the invention, there is a vibration detector array comprising a number of sensor units arranged in a regular and substantially planar configuration, and with separate signal wires going out from each separate sensor unit. The vibration detector array according to this aspect of the invention is characterized in that each sensor unit is such as stated in one of the above mentioned embodiments with a bubble design, and that a plurality of bubbles are arranged in close juxtaposition, with welding rims that are common for neighbor bubbles.

In accordance with one further aspect, the present invention comprises a use of at least one vibration detector array such as stated in the previous sections, as a part of a piece of clothing that can be worn by a person for carrying out a mapping auscultation examination.

A further aspect of the invention comprises a use of at least one vibration detector array such as stated in the previous sections, as a mat or a belt for industrial vibration pickup analysis, the mat/belt being equipped with suitable means for attachment.

A BRIEF DESCRIPTION OF THE DRAWINGS

Figure 2:
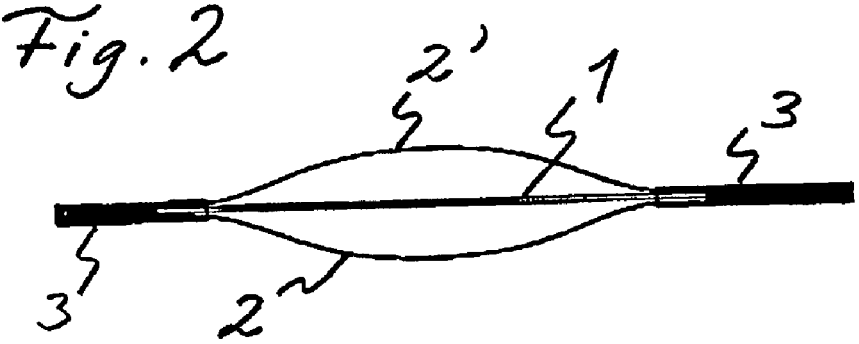
Figure 3:
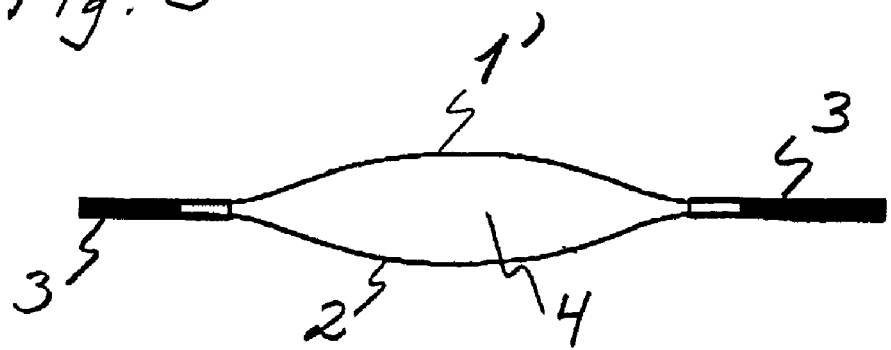
Figure 6:
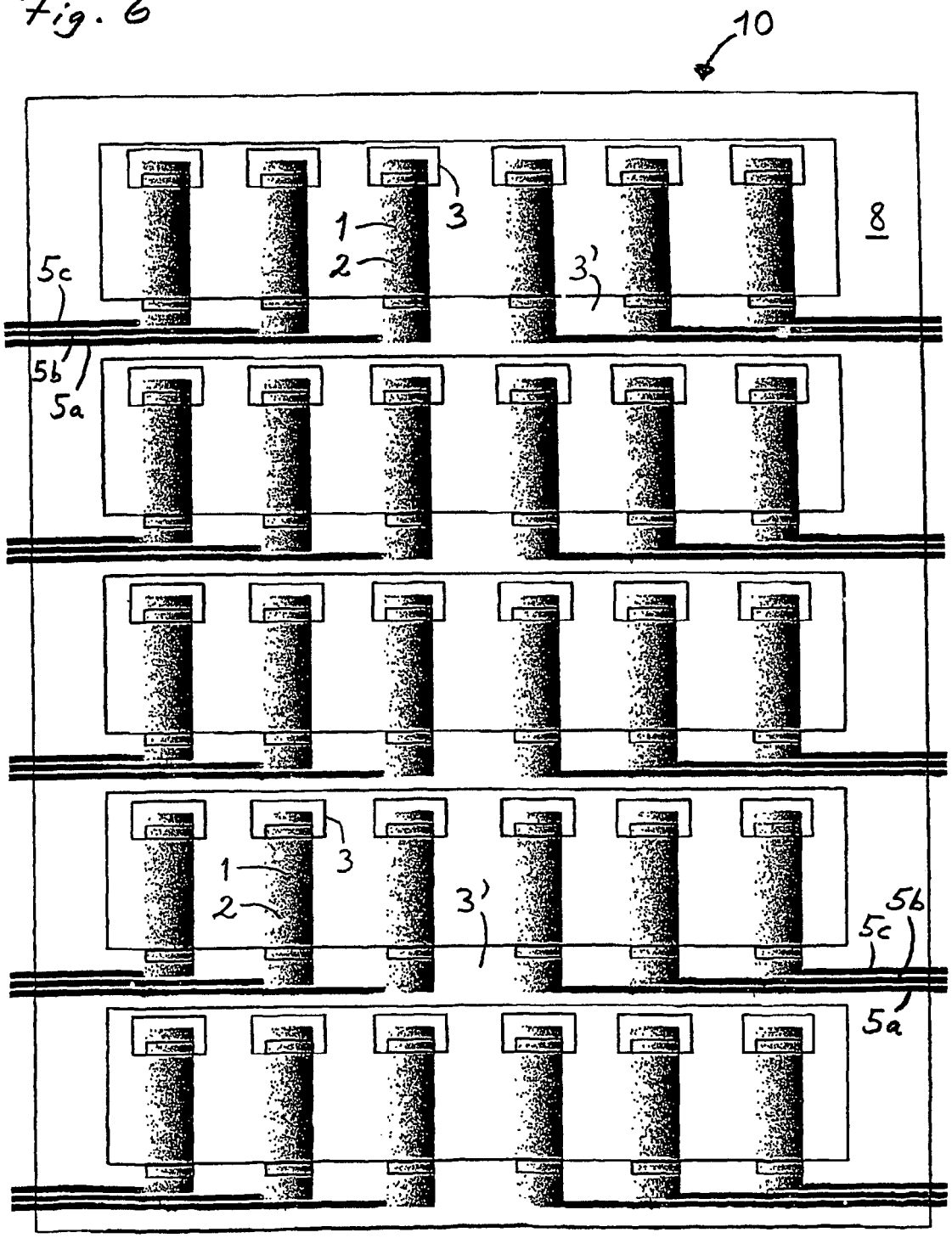
Figure 7A:
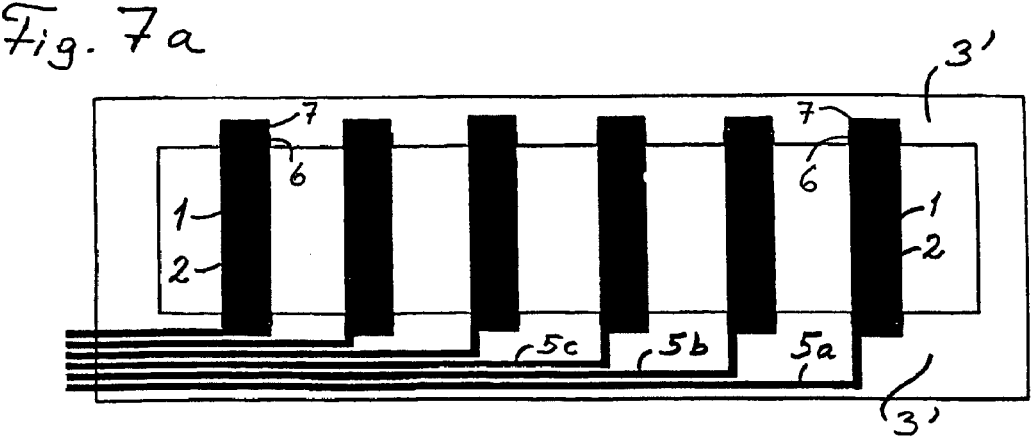
Figure 8:
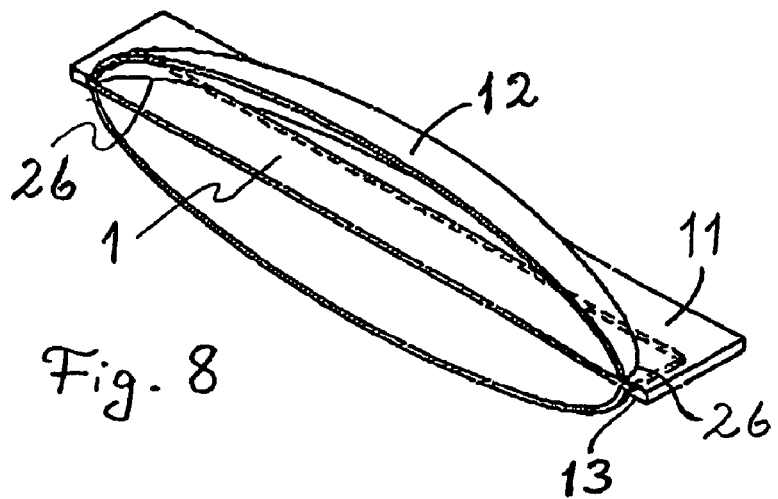
Figure 9:
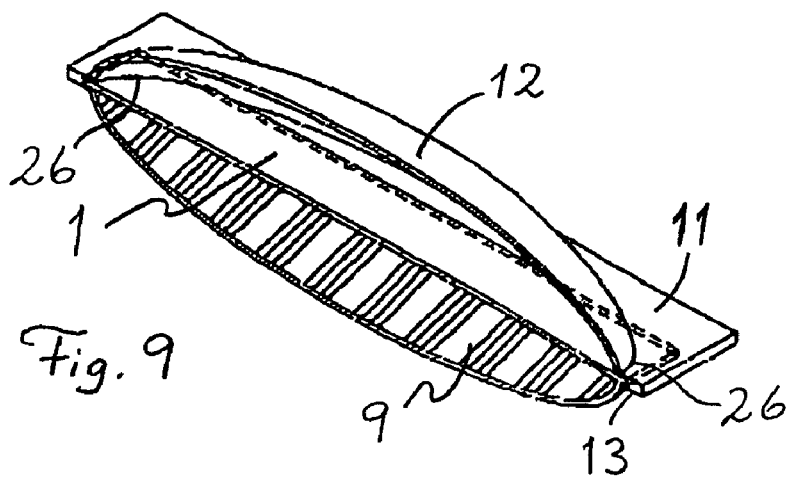
Figure 10:
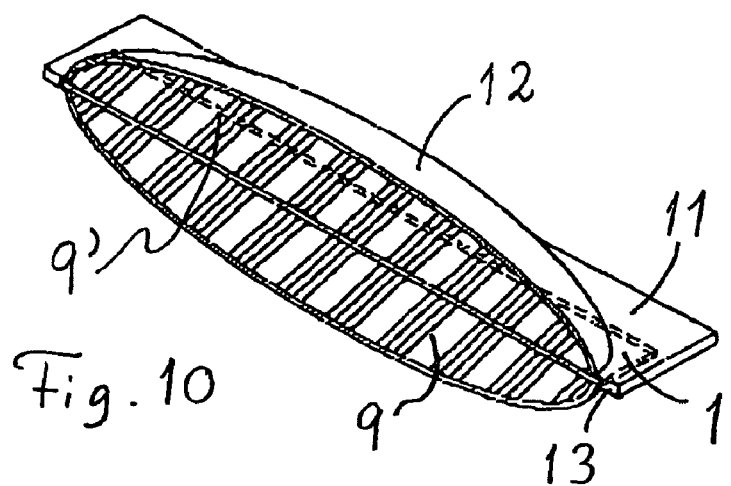
Figure 11A:
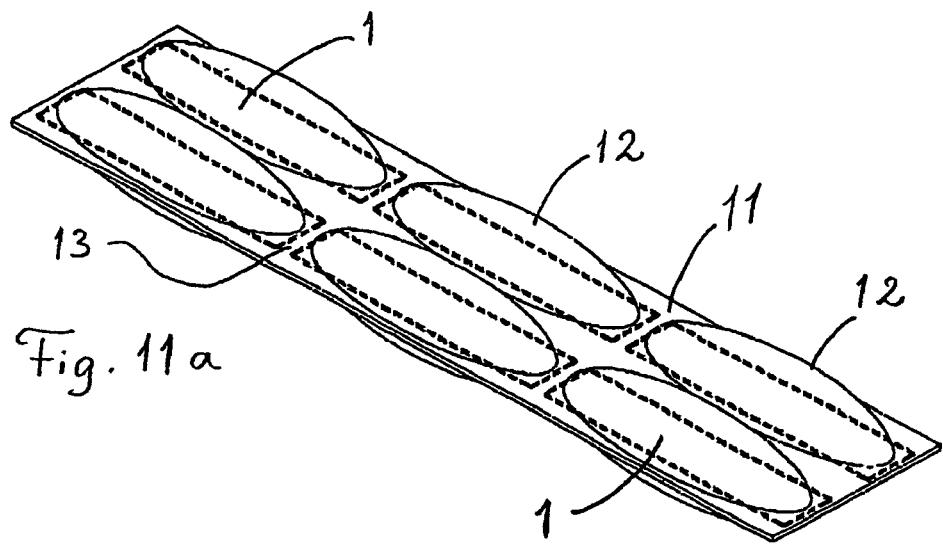
Figure 11B:
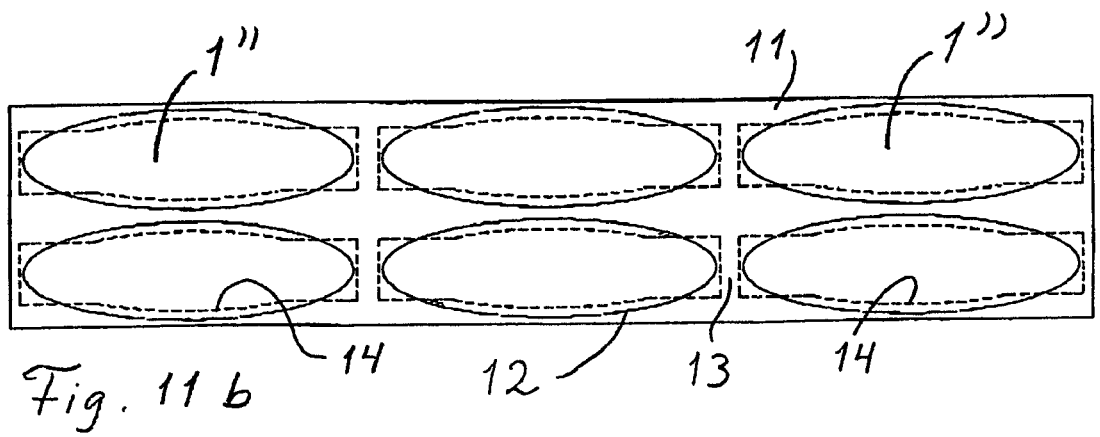
Figure 12:
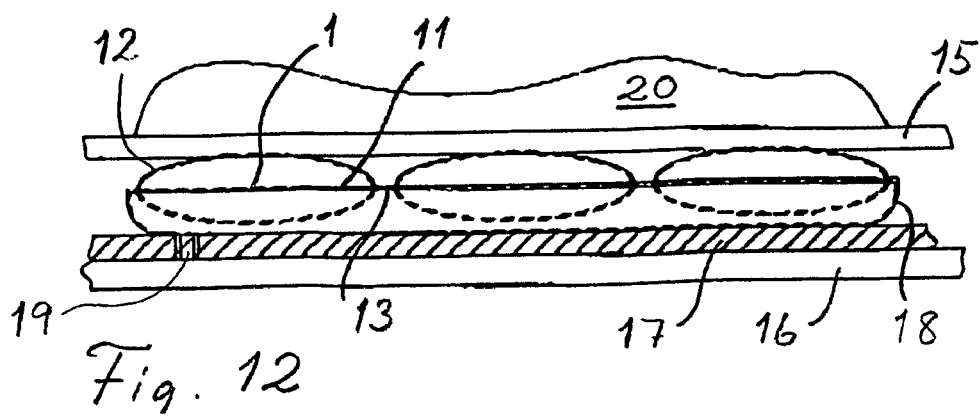
Figure 13:
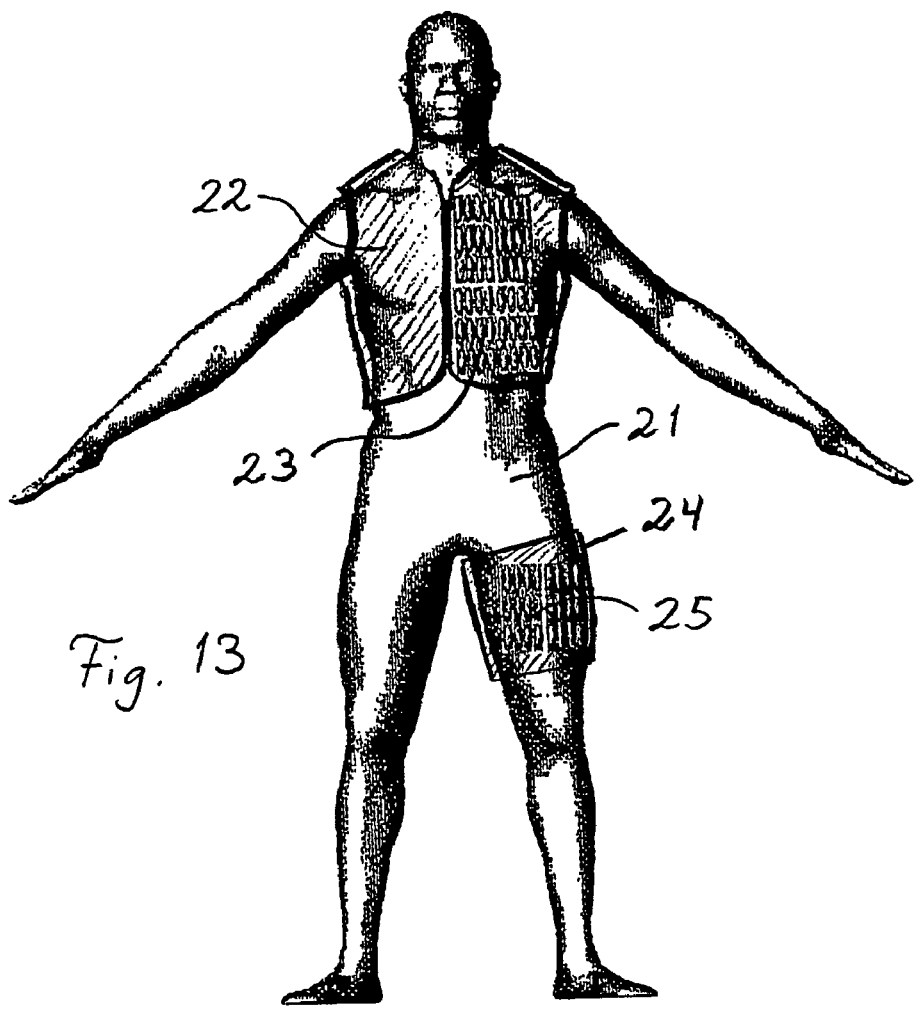
Figure 14:
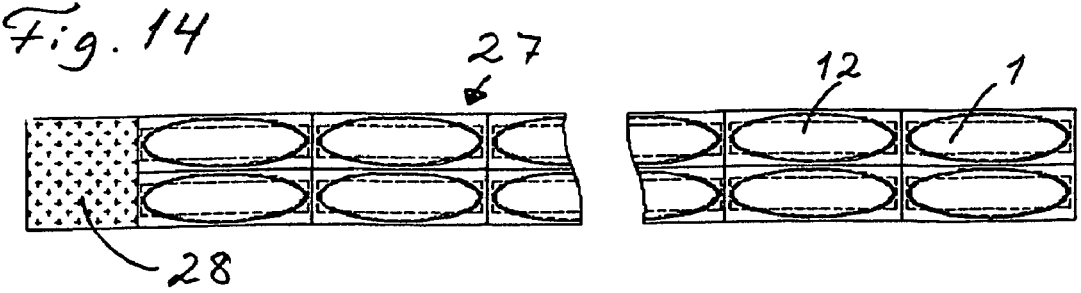

In the following, the invention shall be described in closer detail by going through some exemplary embodiments, and in this connection reference is made to the appended drawings, of which:

FIG. 1 is an elevation view showing a basic embodiment of a sensor unit in accordance with the present invention, as seen laterally in cross section with a piezo-foil strip and a plastic strip, FIG. 2 shows, in a corresponding manner to FIG. 1, an embodiment having a central piezo-foil strip and plastic strips on both sides of the piezo-foil, FIG. 3 shows, in a corresponding manner to FIGS. 1 and 2, an embodiment with a plastic foil strip together with an outwardly curved piezo-foil strip and a silicone substance between the foils, FIG. 4 shows, in a top view, an example of the appearance of a sensor unit in accordance with one of FIGS. 1 and 2, FIG. 5 shows an example of the attachment of strip ends in an end piece for a sensor unit, enlarged and in a view from the side, FIG. 6 shows how a number of sensor units may be arranged in matrix shape in a frame, FIGS. 7a and b show an alternative manner of attachment for sensor units in a frame, FIG. 8 shows an embodiment with a sensor unit of a bubble type, with a piezo-foil strip centrally arranged and air inside the bubble, in a perspective view and with one half of the bubble cut away, FIG. 9 shows, in the same manner as FIG. 8, an alternative bubble embodiment with a substance on one side of the piezo-foil strip and air on the other side, FIG. 10 shows another bubble alternative with substances on both sides of the piezo-foil strip, FIGS. 11 a and b show sheets containing bubble collections, FIG. 12 shows, in a sectional side view, a bubble sheet with extra equipment in the form of an inflatable sound barrier pad and external cladding sheets, FIG. 13 shows, sketch-like, how bubble sheets or sensor unit matrix frames can be arranged in pieces of clothing, and FIG. 14 shows a belt-shaped sensor mat for industrial applications.

DETAILED DESCRIPTION OF THE INVENTION

FIG. 1 illustrates a first and basic embodiment of the invention, namely a sensor unit with a piezoelectric foil strip 1 that is attached at both ends to fiat support parts 3 that constitute end pieces. An engagement strip 2 extends along piezo strip 1, and in the embodiment shown, strip 2 is a lithe longer than piezo strip 1, so that the center of strip 2 bulges a little outward. Strip 2 can also be fixed at both ends to the support parts 3, but it may equally well simply be inserted into a pocket (6, see FIGS. 4 and 5) in the support parts, at both ends or at one end.

The piezo-foil strip 1 may for instance have external measurements of 6×1 cm², these values not constituting any limitation, and the foil itself may be delivered off the shelf. A typical foil thickness may be in the range 28-56 μm, however these values shall not constitute any limitation.

The engagement strip 2 may also be a thin foil, preferably a foil that is a little stiff, unless the space between the two strips 1, 2 is occupied by a substance (see below). Such a foil strip 2 can be made of a plastic material, possibly a rubber material, a thermo foil, a textile material or another material.

The mode of operation for the sensor unit is that the engagement strip 2 is brought into engagement with the surface of a body to be listened to, and sound/vibrations in the body may then propagate to the piezo-foil 1 in two ways, depending on for example the stiffness of the engagement strip 2. Firstly, sound/vibration may propagate right through the engagement strip 2 to reach piezo strip 1 directly. Secondly, vibrations that are transmitted to a stiff engagement strip 2, may cause a vibrating tension in piezo strip 1 via the support parts 3, which support parts are then vibrated toward each other and apart by strip 2. For instance, when listening to machine parts, it is possible to use a rather stiff and curved aluminium plate of e.g. 1 mm thickness as engagement strip 2 in the sensor unit. (Numerical values and material specifications are stated only as non-limiting examples.)

Signal wires from piezo strip 1, i.e. one wire from each side of the piezo-foil, lead out through a support part 3. In the embodiment shown, the support parts 3 are relatively stiff, flat and made from an electrically insulating material, for instance a casting material like plastic (for example polyurethane), glue, stiff cardboard, gore-tex, plaster/tape, or possibly two metal layers with insulation there-between. Piezo-foil strip 1 is attached to each support part 3 by clenching, gluing or attaching in a similar manner, two flat parts of the support part, with the piezo-foil pinched therebetween.

FIG. 2 illustrates a second embodiment of the sensor unit in accordance with the invention. The only difference relative to the embodiment shown in FIG. 1, is the provision of an extra engagement strip 2' on the other side of piezo strip 1, in such a manner that the configuration becomes symmetrical if strips 2 and 2' are made from the same material and have the same length. However, this embodiment shall not be limited to a symmetrical construction. With a symmetrical configuration, however, any one of the two sides of the sensor unit can be chosen for engagement with the body to be listened to. Piezo strip 1 can also be tensioned by applying a pressure to the outer strip (e.g. 2') that does not engage the body to be listened to.

FIG. 3 illustrates a somewhat different variant of the sensor unit in accordance with the invention. In this case, a piezoelectric foil strip 1' and an engagement foil strip 2 are both fixedly fastened in support parts 3, and in between them a silicone substance 4 has been loaded, to keep the two foils 1', 2 apart such as shown in the drawing. The silicone substance can be replaced by some other substance having at least an equally high viscosity and similar pressure transmission characteristics, i.e. a substance that is equally solid or an even more solid substance.

It must be noted that in the embodiments as shown in FIGS. 1, 2 and 3, the sensor units are, as a starting point, open at the sides (i.e., in a direction out of and into the drawing sheet). This means that in the embodiment of FIG. 3, the substance 4 must be sufficiently solid not to flow out at the sides of its own accord. (In the embodiments in FIGS. 1 and 2, there is only air between the strips.) But the embodiments of FIGS. 2 and 3 will also lead in a natural manner to closed embodiments, i.e. bubble-shaped embodiments that will be discussed below.

FIG. 4 illustrates a sensor unit in accordance with FIG. 1 or FIG. 2 in a view from above, and the same reference numerals are still used for the same elements. Reference numeral 5 designates signal wires leading out from the piezo strip, reference numeral 6 designates insertion pockets for engagement strips 2, 2', and fastening areas for piezo strip 1 are designated by reference numeral 7.

FIG. 5 shows, enlarged and in partial elevation, a support part 3 with an insertion pocket 6, a fastening area 7 and engagement strips 2 and 2' entering pocket 6. In this embodiment, two piezo strips 1 enter support part 3 and are fixed in area 7. The purpose of using several piezo strips at the same time is to change the capacitance and to obtain other signal strength values.

As mentioned in the introduction, a main purpose of the sensor unit in accordance with the invention is to constitute part of larger groups of such units. FIG. 6 shows one example among many possible ones, both with regard to number and array structure, of an arrangement of sensor units in a two-dimensional array 10, for use in computer-assisted auscultation, with sound recording from a body through a large surface area. In the example, a frame 8 appears, in which frame there are arranged thirty sensor units in accordance with one of the previously mentioned embodiments, and the sensor units are arranged in a regular 5×6 matrix array. In the embodiment shown, each sensor unit has an end with a separate (individual) support part 3 "hanging freely" in an open space in the frame, while all six sensor units in one such open space are attached to one and the same elongated support part 3' that constitutes a cross-arm internally in frame 8. Hence, frame 8 contains four internal cross-arms 3' of this type, and additionally, the lower frame edge is also a common support part 3' of this type for six sensor units. It appears also that signal wire pairs 5a, 5b, 5c exit along the support parts 3', i.e. one pair from every single sensor unit.

Such a sensor array sheet 10 can be laid engagingly toward a surface to be listened to, or attached thereto, or it can be sewn or welded into a garment or a garment part that is suitable to be slipped onto or attached to the body of a patient for auscultation examination, see FIG. 13.

Figure 7B:
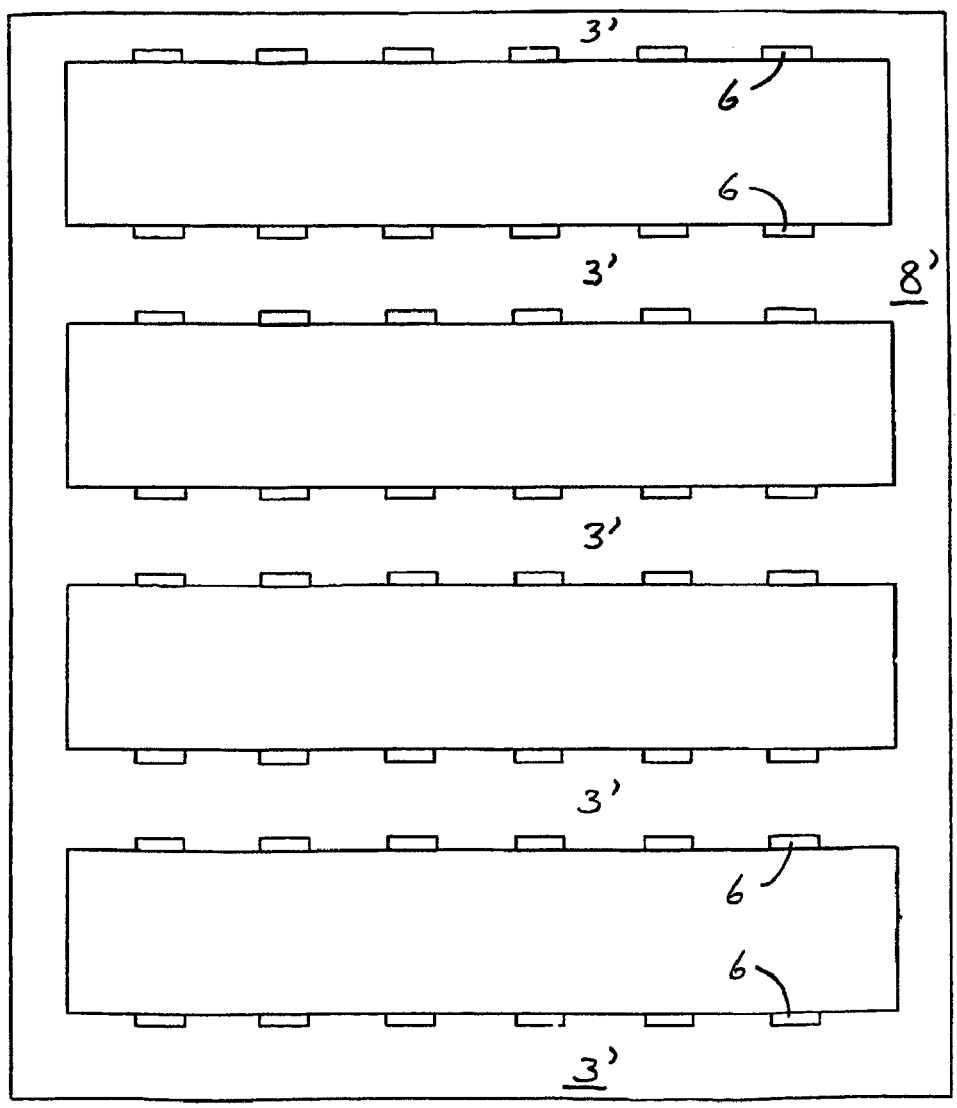

FIGS. 7a and 7b illustrates an embodiment that is a little different from the embodiment shown in FIG. 6, namely in the fact that each sensor unit is attached fixedly to frame 8' at both ends (i.e., the support parts 3' are in this case common "everywhere" to six sensor units arranged in a row). Thus, in FIG. 7a, one such row of sensor units is shown in accordance with one of the previously mentioned embodiments, but in this case the sensor units are arranged with common support parts 3' at both sides. For the rest, the reference numerals in FIG. 7a designate elements in a corresponding manner as previously. FIG. 7b illustrates a complete frame 8' merely with indications (actually insertion pockets 6) of seating locations for single sensor units in the frame. Hence, in this case, the piezo strip of every sensor unit will be attached fixedly to the frame at both ends.

In the embodiment appearing in FIG. 6, i.e. with sensor units that are free at one end, an outer pressure will be necessary to provide good signals from the listening object. In comparison, the embodiment shown in FIG. 7 provides a frame-bound support of single sensors, and it can be used with precision for monitoring a certain area, since the sides of the frame represent the pressure (i.e. through the selected pressure of the frame sides against the surface of the listening object when the frame is attached/fastened).

As previously mentioned in connection with FIGS. 2 and 3, an alternative embodiment is of a type that is closed laterally. FIGS. 8, 9 and 10 illustrate alternative but related embodiments of sensor units in accordance with the invention, which sensor unit embodiments are suitable to constitute parts of larger "bubble sheets". A sensor unit of the simplest bubble type appears in FIG. 8 (i.e., FIG. 8 shows a section of a bubble in a perspective view). The bubble consists of two distended (inflated) bubble halves 12 meeting along a welding rim 26 that defines an oval/elliptical opening in a planar sheet 11. A piezo strip 1 of the same type as mentioned previously, is attached at its two ends in welding rim areas 13 in sheet 11, and extends across the oval/elliptical opening in the sheet. Hence, above and below the opening in sheet 11, which opening contains a cross-over piezo strip 1, curved strips 12 rise in the form of bubble halves delimiting a closed space surrounding the piezo strip 1. Inside the space there is air or possibly some other gas.

In FIG. 9, a substance 9 has been brought in at one side of piezo strip 1 in a bubble shaped similarly to that shown in FIG. 8, and in a similar manner to that shown in FIG. 3. Further, in FIG. 10, substances 9, 9' have been laid in at both sides of the piezo strip. The substances may be silicone substance, a gel, rubber or a metallic material. (In the last mentioned case, it must be mentioned that it is not possible to use an electrically conducting substance on both sides of the piezo strip, because of the possibly of short-circuiting the piezo foil.)

As previously mentioned, the substances should not be too "thin" (i.e., they should be sufficiently solid), so that they will stay at respective sides of the piezo strip even though the strip does not divide the bubble space in two closed halves. It should be noted, however, that the piezo strip may be shaped with a lateral extension in the central part, in order to better cover the sheet opening (see the shape in FIG. 11b). The central area of the piezo strip must be free, in order to obtain a good signal from the strip. Therefore, attachment of the strip 1 to the side edges can normally not be made without at the same time having precise control over the elastic characteristics of the bubble wall. But in such an embodiment, it will be possible to separate the two substances completely, and then it will be possible to also use more "thin" substances, possibly also different gases at each side of the piezo strip.

FIG. 11a illustrates an assembly of single bubble sensor units in a sheet 11 of larger size, however not larger than two by three bubbles. FIG. 11b shows an equally large bubble sheet 11, in which the separate piezo strips 1" have an extended central part with a side edge 14 that curves out toward the side edge of the opening/the bubble wall. But a small clearance still remains between strip 1" and the bubble wall in this case.

FIG. 13 illustrates two examples of garments or garment-like units, into which unit bubble sheets or sensor matrix sheets can be built. A person 21 in the figure wears in an upper position a vest 22 having a bubble sheet or a sensor matrix sheet 23 attached therein, and another embodiment in the form of a thigh bandage 24 is also equipped with a matrix 25 of sensor units. This may be a matter of auscultation regarding heart or lung function using the vest 22, and of listening to an artery with the bandage 24. A gathering cable (not shown) will carry signals to a (not shown) computer that interprets the signals and generates a suitable display. Simpler types of garments can be of interest. It is for instance possible to provide mat or belt shaped garments that have a sensor bubble or sensor matrix sheet across a substantial part of their surface. Such mat/belt shaped garments may then have attachment means in the form of elastic areas with velcro.

FIG. 12 shows, in a sectional view through a bubble sheet, various extra equipment that is possible and that may be of interest in connection with auscultation examinations. Reference numeral 20 designates the topical listening object. A sound-transparent material, for instance silk fabric, synthetic fabric, or cloth, is shown by reference numeral 15, and forms a surface between the actual bubble sheet 11 and the object 20. On the outside (underside) of the bubbles, inflatable/fillable pads or fields 18 are arranged, with a valve 19. A number of bubbles can be covered by such a pad, which has for its purpose to provide shape adaptation against a body or similar. Reference numeral 17 designates a noise barrier layer. This may relate to screening against incident electromagnetic radiation, and electrically conductive material is then used. It may also be of interest to screen against external sounds/vibrations, and then a sound-absorbing substance will be used, for instance felt or similar. It may be of interest to use both types of screening at the same time. Finally, layer 16 constitutes an outer cover, which may be related to design, and which may consist of for instance a textile, oil skin, goretex or other material.

As regards types of substances that should possibly be used in bubble sheets, an embodiment of interest would be that the bubbles in the half that faces e.g. a body part to be listened to, contains a substance having hardness (i.e. "Shore"-number) adapted to the hardness of the body tissue in and just under the skin, in order to obtain adaptation with regard to acoustic impedance. In the outer half of the bubbles, air might be chosen. Such a configuration makes it easier to separate sound (noise) received from the surroundings, from the signals of interest.

FIG. 14 illustrates an example of an industrial "belt" or "mat" embodiment of a sensor matrix sheet or bubble sheet, or actually a bubble sheet which has been drawn in the shape of a belt 27. Belt 27 is equipped with an attachment device 28 which in this case is an elastic area with velcro, but an attachment device in the form of bands, hooks, buttons etc. can be provided in topical cases. The belt/mat shall be strapped down to a construction part in order to make it possible to listen through an engagement surface, with regard to sound/vibration analysis of underlying structures.

Finally, it should also be mentioned that the possibility exists to provide sensor matrix sheets and bubble sheets with a further combination effect with regard to auscultation examination of a patient. It will actually be possible to combine electrodes for engagement directly against the skin surface of a patient, for instance on 5-6 special sensor elements among 40-50 elements in a sheet, in order to make a simultaneous ECG examination. This means then that, as previously mentioned, the strip 2 in these special sensor units may be of metal, and connected in a special manner for transporting out electrical signals received from the body. In the case with bubbles, the special sensor bubbles intended for the ECG, may then have metallization or through electrodes for contacting the skin. In the previously mentioned case with an electrically conductive substance in one half of a bubble, further transmission of a signal may then possibly be effected through this conductive substance, or separate wiring may be arranged.

The invention claimed is:

1. A sensor unit for picking up mechanical vibrations, sounds, and ultrasound from a surface of a body, comprising:
   a piezoelectric foil strip defining a sensor element, said piezoelectric strip having signal wires attached thereto for transmitting electrical signals representing the vibrations, sounds, or ultrasound to be picked up;
   flat support parts for holding only opposite ends of said piezoelectric strip; and
   an engagement strip for engaging the surface of the body to receive vibrations therefrom, and for propagating the vibrations to said piezoelectric strip, said engagement strip being held in said support parts so as to extend in a curved manner along said piezoelectric strip and define a space between said piezoelectric strip and said engagement strip.

2. The sensor unit of claim 1, wherein said support parts are separate support pieces having holding pockets receiving one of said opposite ends of said piezoelectric strip.

3. The sensor unit of claim 2, wherein said engagement strip is stiff and curved so as to tension said piezoelectric strip.

4. A vibration detector array comprising:
   a plurality of sensor units arranged in a substantially planar A by B matrix with A units arranged along a first direction, and B units in a second direction perpendicular with respect to the first direction and within the same plane, each of said sensor units comprising a sensor unit as recited in claim 2;
   separate signal wires leading out from each of said plurality of separate sensor units; and
   a frame to which each of said plurality of sensor units is attached.

5. The vibration detector array of claim 4, wherein said frame has B parallel openings in which a first end of each of A sensor units is mounted by a common support piece corresponding to one of said support parts, said common support piece defining a boundary edge for each of said B parallel openings, a second end of each of said A sensor units hanging freely.

6. A method of using a vibration detector, comprising:
   incorporating said vibration detector array as recited in claim 4 into a garment; and
   having a person wear the garment for carrying out a surveying auscultation examination of the person.

7. A method of using a vibration detector, comprising:
   incorporating said vibration detector array as recited in claim 4 into a belt having an attachment device; and
   attaching the belt to an object for industrial vibration pickup analysis of the object.

8. The sensor unit of claim 1, wherein said engagement strip constitutes a first engagement strip, further comprising a second engagement strip, said first engagement strip and said second engagement strip being located on opposite sides of said piezoelectric strip.

9. The sensor unit of claim 8, wherein each of said first engagement strip and said second engagement strip is stiff and curved so as to tension said piezoelectric strip.

10. A vibration detector array comprising:
    a plurality of sensor units arranged in a substantially planar A by B matrix with A units arranged along a first direction, and B units in a second direction perpendicular with respect to the first direction and within the same plane, each of said sensor units comprising a sensor unit as recited in claim 8;
    separate signal wires leading out from each of said plurality of separate sensor units; and
    a frame to which each of said plurality of sensor units is attached.

11. The sensor unit of claim 2, wherein said engagement strip is stiff and curved so as to tension said piezoelectric strip.

12. The sensor unit of claim 11, wherein said engagement strip is loosely attached to one of said support parts by being inserted into a pocket of said one of said support parts.

13. The sensor unit of claim 1, wherein the space between said piezoelectric strip and said engagement strip is filled with a substance operable to transfer pressure, said piezoelectric strip and said engagement strip having central areas substantially symmetrically outwardly curved so as to maintain said substance in place.

14. The sensor unit of claim 1, wherein said support parts comprise welding rims, said engagement strip comprises a first semi-ovoid foil piece, further comprising a second semi-ovoid foil piece, said first semi-ovoid foil piece and said second semi-ovoid foil piece having opposite ends held by said welding rims so as to define a bubble shape.

15. A vibration detector array comprising:
a plurality of sensor units arranged in a substantially planar configuration, each respective sensor unit having separate signal wires leading out therefrom, each of said sensor units comprising a sensor unit as recited in claim 14, said sensor units being arranged in close juxtaposition so that adjacent sensor units share a common welding rim.

16. The sensor unit of claim 14, wherein said piezoelectric strip is stretched in a space defined between said first semi-ovoid foil piece and said second semi-ovoid foil piece, and is located midway between said first semi-ovoid foil piece and said second semi-ovoid foil piece.

17. The sensor unit of claim 16, wherein at least one of a space defined between said first semi-ovoid foil piece and said piezoelectric strip and a space defined between said second semi-ovoid foil piece and said piezoelectric strip is filled with a substance operable to transfer pressure.

18. The sensor unit of claim 17, wherein said substance has a hardness value of the same magnitude as body tissue in an area in and under skin of a topical listening area of a human body or animal body.

19. The sensor unit of claim 1, wherein only opposite ends of both said piezoelectric strip and said engagement strip are fixed to said support parts such that each opposite elongated side of said sensor unit is open, further comprising a viscous silicone substance between said piezoelectric strip and said engagement strip.

20. A vibration detection device comprising:
a garment to be worn by a person; and
a vibration detection array incorporated into said garment, said array including:
a plurality of separate sensor units arranged in a substantially planar manner, each of said sensor units comprising a sensor unit as recited in claim 1;
separate signal wires leading out from each of said plurality of separate sensor units; and
a frame to which each of said plurality of sensor units is attached.

* * * * *